United States Patent
McDavid, III

[11] Patent Number: 5,797,865
[45] Date of Patent: Aug. 25, 1998

[54] LIGHTWEIGHT ANKLE RESTRAINT

[75] Inventor: Robert Finley McDavid, III, Downers Grove, Ill.

[73] Assignee: McDavid Knee Guard, Inc., Chicago, Ill.

[21] Appl. No.: 931,592

[22] Filed: Sep. 16, 1997

[51] Int. Cl.$^6$ ............................................. A61F 5/00
[52] U.S. Cl. ............................................. 602/27; 602/16
[58] Field of Search ........................ 602/5, 16, 23, 602/27–29; 128/882

[56] References Cited

U.S. PATENT DOCUMENTS

| | | |
|---|---|---|
| Re. 15,446 | 9/1922 | Hamilton. |
| Re. 33,395 | 10/1990 | Peters. |
| 112,952 | 3/1871 | Niswander. |
| 130,639 | 8/1872 | Howe. |
| 1,381,290 | 6/1921 | Diadul, Jr. |
| 2,516,872 | 8/1950 | Hauser et al. |
| 3,086,521 | 4/1963 | Desai et al. |
| 4,144,581 | 3/1979 | Chappell. |
| 4,320,748 | 3/1982 | Racette et al. |
| 4,510,927 | 4/1985 | Peters. |
| 4,517,968 | 5/1985 | Greene et al. |
| 4,587,962 | 5/1986 | Greene et al. |
| 4,665,904 | 5/1987 | Lerman. |
| 4,693,239 | 9/1987 | Clover, Jr. |
| 4,719,926 | 1/1988 | Nelson. |
| 4,771,768 | 9/1988 | Crispin. |
| 4,809,686 | 3/1989 | Crane. |
| 4,962,760 | 10/1990 | Jones .............................. 602/27 |
| 5,007,416 | 4/1991 | Burns et al. |
| 5,014,690 | 5/1991 | Hepburn et al. |
| 5,031,607 | 7/1991 | Peters. |
| 5,044,360 | 9/1991 | Janke. |
| 5,069,202 | 12/1991 | Prock. |
| 5,070,868 | 12/1991 | Hepburn et al. |
| 5,086,760 | 2/1992 | Neumann et al. ............... 602/27 |
| 5,092,321 | 3/1992 | Spademan ........................ 602/27 |
| 5,094,232 | 3/1992 | Harris et al. ..................... 602/16 |
| 5,156,630 | 10/1992 | Rappoport et al. .............. 623/47 |
| 5,176,623 | 1/1993 | Stetman et al. .................. 602/27 |
| 5,183,036 | 2/1993 | Spademan ........................ 602/10 |
| 5,209,722 | 5/1993 | Miklaus et al. .................. 602/27 |
| 5,242,378 | 9/1993 | Baker ............................... 602/23 |
| 5,242,379 | 9/1993 | Harris et al. ..................... 602/27 |
| 5,250,021 | 10/1993 | Chang .............................. 602/27 |
| 5,328,444 | 7/1994 | Whiteside ........................ 602/16 |
| 5,366,439 | 11/1994 | Peters .............................. 602/27 |
| 5,372,574 | 12/1994 | Hino et al. ....................... 602/16 |
| 5,399,152 | 3/1995 | Habermeyer et al. ........... 602/23 |
| 5,429,588 | 7/1995 | Young et al. .................... 602/27 |
| 5,445,603 | 8/1995 | Wilkerson ....................... 602/27 |
| 5,503,622 | 4/1996 | Wehr ................................ 602/27 |
| 5,571,078 | 11/1996 | Malewicz ........................ 602/27 |
| 5,630,792 | 5/1997 | Neal ................................. 602/27 |
| 5,676,642 | 10/1997 | Peters .............................. 602/27 |

*Primary Examiner*—Linda C. Dvorak
*Attorney, Agent, or Firm*—Fitch, Even, Tabin & Flannery

[57] ABSTRACT

An ankle restraint is made of plastic material and includes a pair of splint plates pivotally joined to struts of a stirrup member. Stops carried on the splint plates interfere with the range of motion of the struts, thereby limiting movement of the wearer's ankle. The stop members have faces engaging edges of the struts and have a height matching the thickness of the struts. Polypropylene or other plastic materials may be used to achieve a desired compromise between a desired flexural modulus and a desired impact strength.

14 Claims, 7 Drawing Sheets

Fig. 4
Fig. 5
Fig. 7
Fig. 9
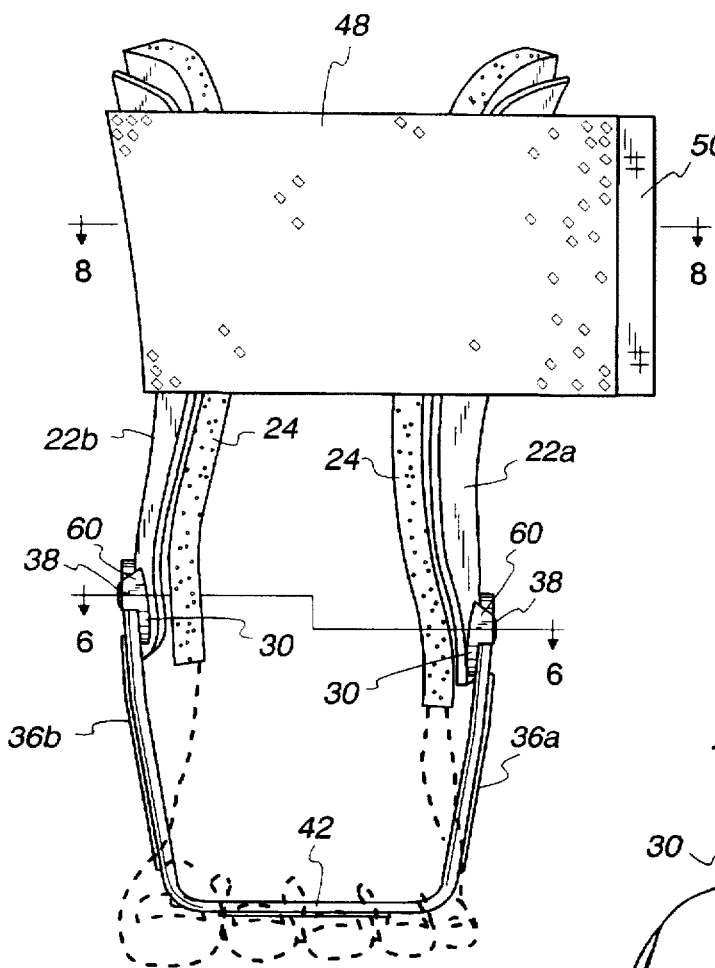
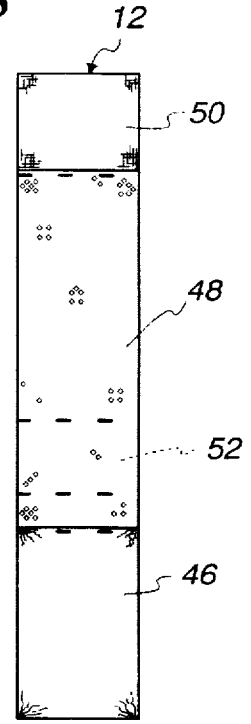
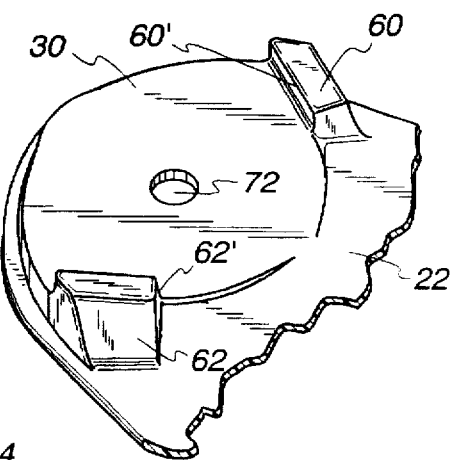
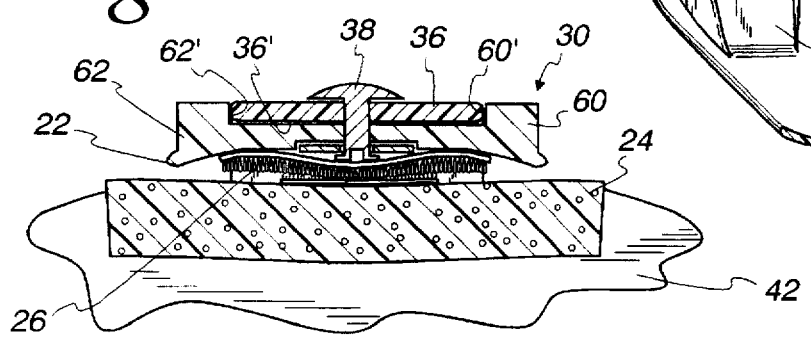

LIGHTWEIGHT ANKLE RESTRAINT

BACKGROUND OF THE INVENTION

1. Field of the Invention

The present invention pertains to ankle restraints which, when worn by a user, limits movement of the ankle in a predetermined manner.

2. Description of Related Art

Over the years, various ankle restraints have been developed for different types of uses. For example, in the medical community, ankle restraints have been employed in the rehabilitation of ankle and foot injuries. The types of devices employed for this purpose differ considerably from ankle restraints developed for use in athletic endeavors. For example, in a medical treatment for rehabilitation of ankle and foot injuries, a rigid cast may be employed to immobilize the wearer's ankle and foot, at least during the initial stages of rehabilitation. Over the years, articulated medical devices have been proposed. These types of devices are principally concerned with providing a well defined range of motion with positive stops to prevent excursion beyond design limits. Typically, such ankle restrains employ metal components, especially for the stop members. While such articulated devices do allow a certain amount of mobility, they are typically too bulky and heavy for athletic endeavors, where there is an interest in maintaining a wearer's full range of motion and to be as unobtrusive as possible. In the medical type of devices, on the other hand, an ankle restraint may operate to remind a wearer that care should be taken during the rehabilitation process. It is not unusual in such instances to require modification to a wearer's shoes and clothing to accommodate the bulky appliance.

In the area of athletic use, on the other hand, a wearer is primarily concerned with competition performance in an unimpeded full range of normal motion is required in order to maintain a competitive edge. Ankle restraints for such use may comprise, for example, athletic tape or woven athletic bandages which are wrapped about a wearer's foot or ankle. Rather than provide a positive stop which cannot be overridden, as in the medical applications, ankle restraints used for athletic purposes are typically relied upon to provide a limited protection against possible ankle injuries, the predisposition for which is anticipated according to the type of athletic endeavor involved. Wearer's of ankle restraints for athletic purposes are usually interested in avoiding bulky or complex apparatus which would require a modification of the user's shoes and clothing. Further, athletic restraints used for athletic purposes should ideally be readily stowable in a gym bag, suitcase or the like.

The use of articulated metallic components or even hard, relatively inflexible components are generally unsuitable for athletic use, because of chafing, pressure points and similar problems suffered during the rigors of a strenuous athletic event, particularly in a competitive event in which contact with other players is possible.

SUMMARY OF THE INVENTION

It is an object of the present invention to provide an ankle restraint for athletic use having articulated components with stop members to limit the range of motion of a wearer's ankle.

Another object of the present invention is to provide an ankle restraint of the above-described type made of non-metallic materials.

A further object of the present invention is to provide an ankle restraint of the above type made of a plastic material which is relatively lightweight and flexible.

A further object of the present invention is to provide an ankle restraint having articulated components with stop members, made of a common plastic material throughout.

Yet another object of the present invention is to provide an ankle restraint of the above-described type which may be worn on either foot.

These and other objects of the present invention which will become apparent from studying the appended description and drawings are provided in a restraint for limiting movement of the wearer's ankle, comprising:

a stirrup member with a monolithic one-piece body having a sole plate and a pair of spaced-apart struts upstanding from the sole plate, the struts having upper free ends with a pair of rounded edge portions;

a pair of leg-engaging splint plates, each having an outer surface and a lower end with a flat surface land portion which extends above the outer surface and which is hingedly connected to the upper end of a respective strut, each splint plate carrying a pair of stop members upwardly and inwardly inclined toward one another, one on either side of the upper free end of said strut;

each strut having opposed generally co-extensive sides, each side having an edge terminating in said rounded edge portion; and said stop members having stop surfaces positioned to engage one side edge of a strut as one of the rounded edge portions moves past the stop surface of the other stop member.

In one of its aspects, the present invention provides a pair of stop members mounted on each splint plate which is secured to a user's leg with a stretch resistant cuff. The stop members interact with edges of struts extending from either side of the sole plate which engages the bottom of a user's foot. The strut edges and stop members coact to limit movement of the struts in opposite directions where the struts are pivotally swung toward the front or rear of a user's foot. The construction is one which prevents the struts from pivoting, relative to the splint plates, more than a predetermined distance. The stop means have a height at least commensurate with the thickness of the strut edge portions contacting the stop members. Further, the stop members are elevated above the splint plate and, when the surface of the splint plate is formed to have a convex shape, the stop members are disposed above the point of maximum curvature of the splint plate surface. In another aspect, the present invention provides a flat surface land portion adjacent the stop members, for pivotal wiping contact with the upper ends of the struts, thus ensuring substantially full edge contact between the strut edges and the stop members free of misaligning movements associated with struts passing over the curved convex surface of the splint plates.

BRIEF DESCRIPTION OF THE DRAWINGS

FIG. 4 is a front elevational view thereof;

FIG. 5 is a top plan view of a strap used therewith;

FIG. 7 is a fragmentary perspective view of the upper portion thereof;

3

Figure 2:
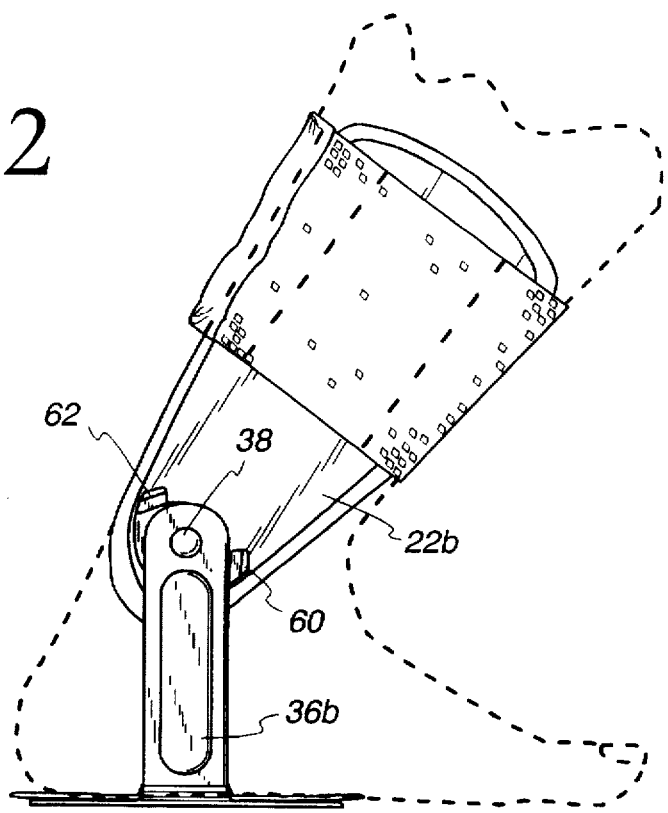
FIGS. 2 and 3 are side elevational views thereof.
Figure 3:
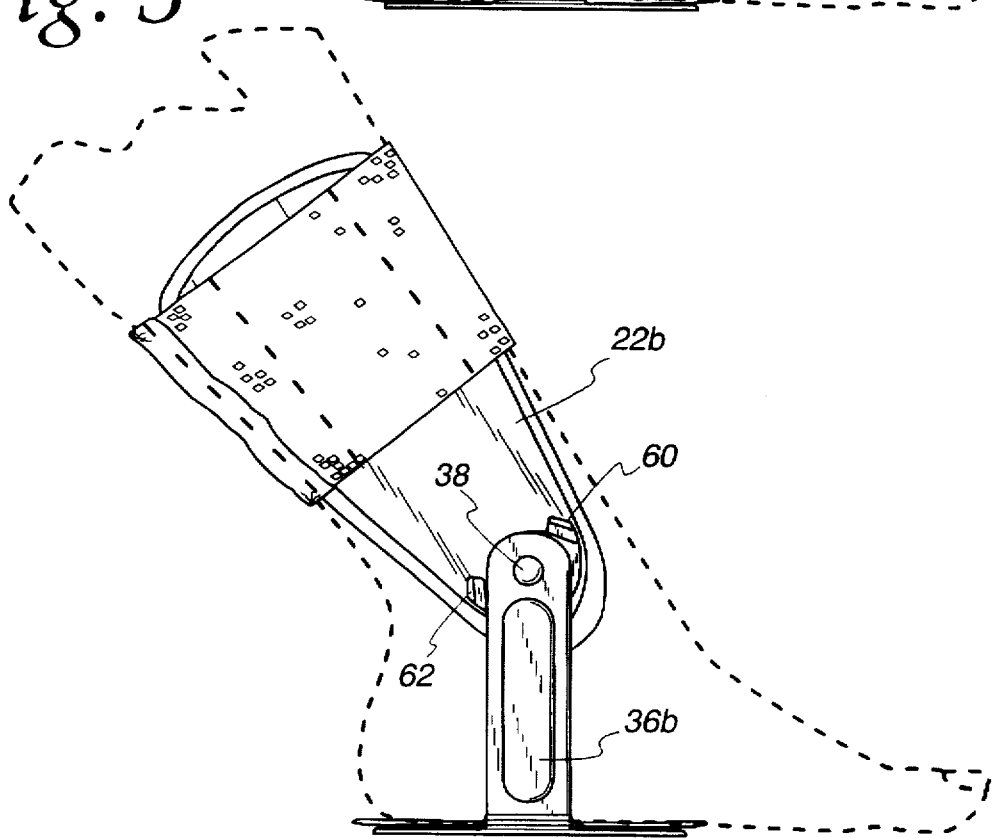
Figure 8:
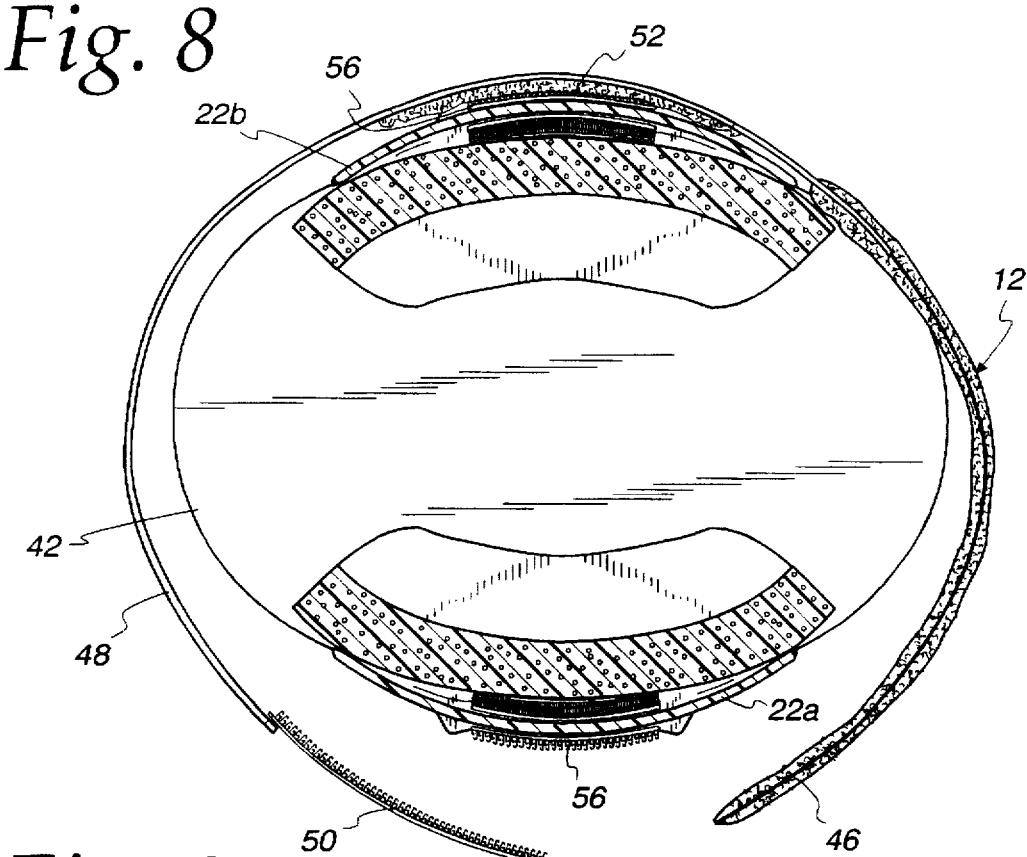
Figure 6:
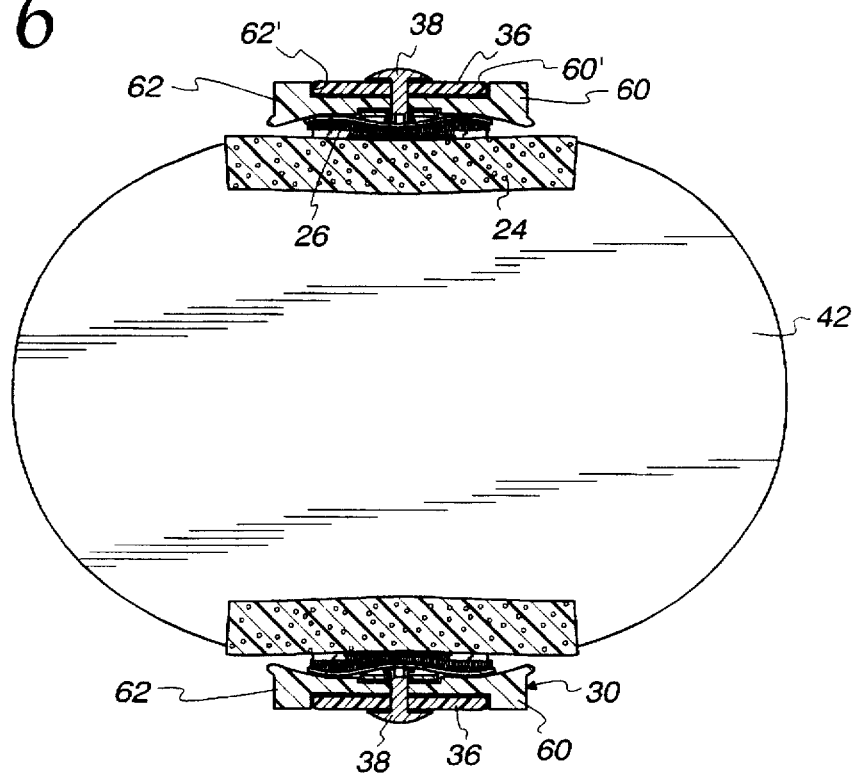
FIG. 6 is a cross-sectional view taken along the line 6—6 of FIG. 4.
Figure 10:
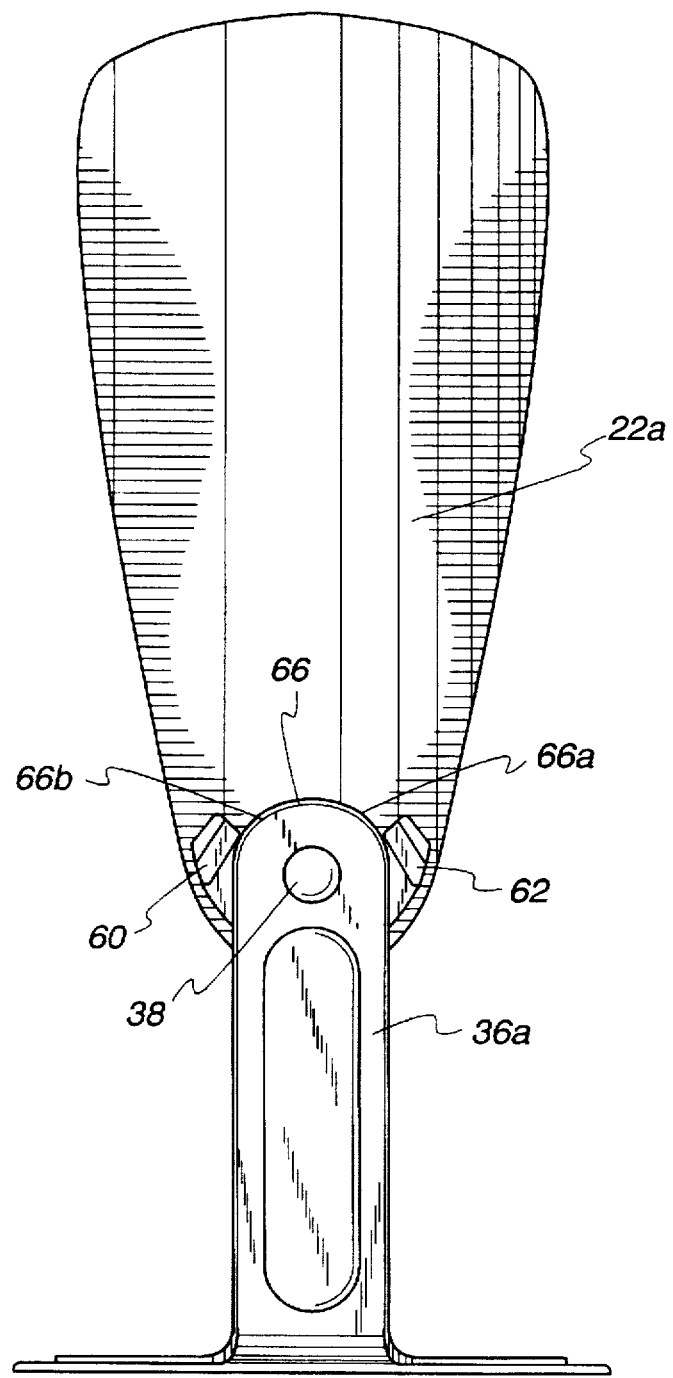
Figure 11:
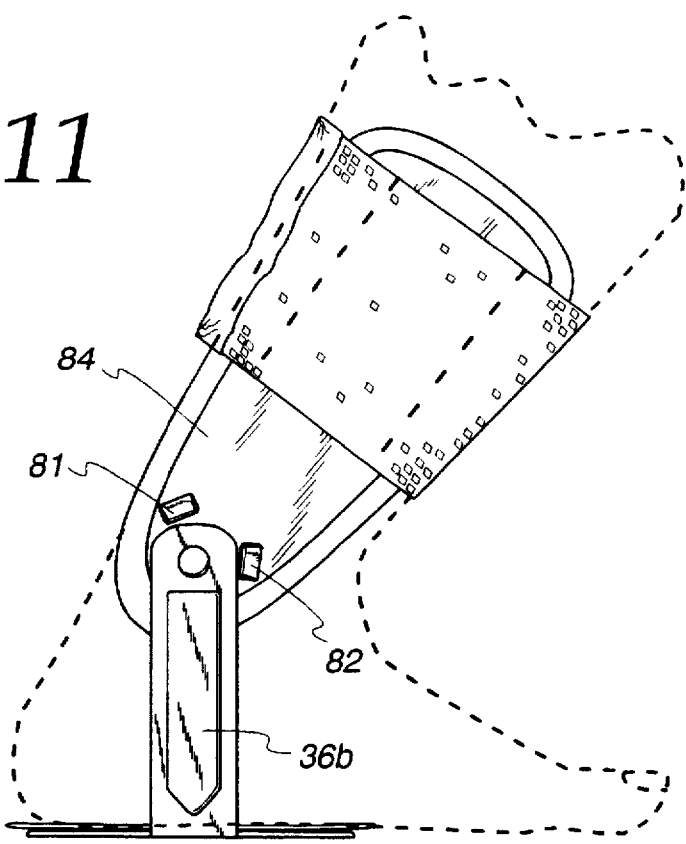
Figure 12:
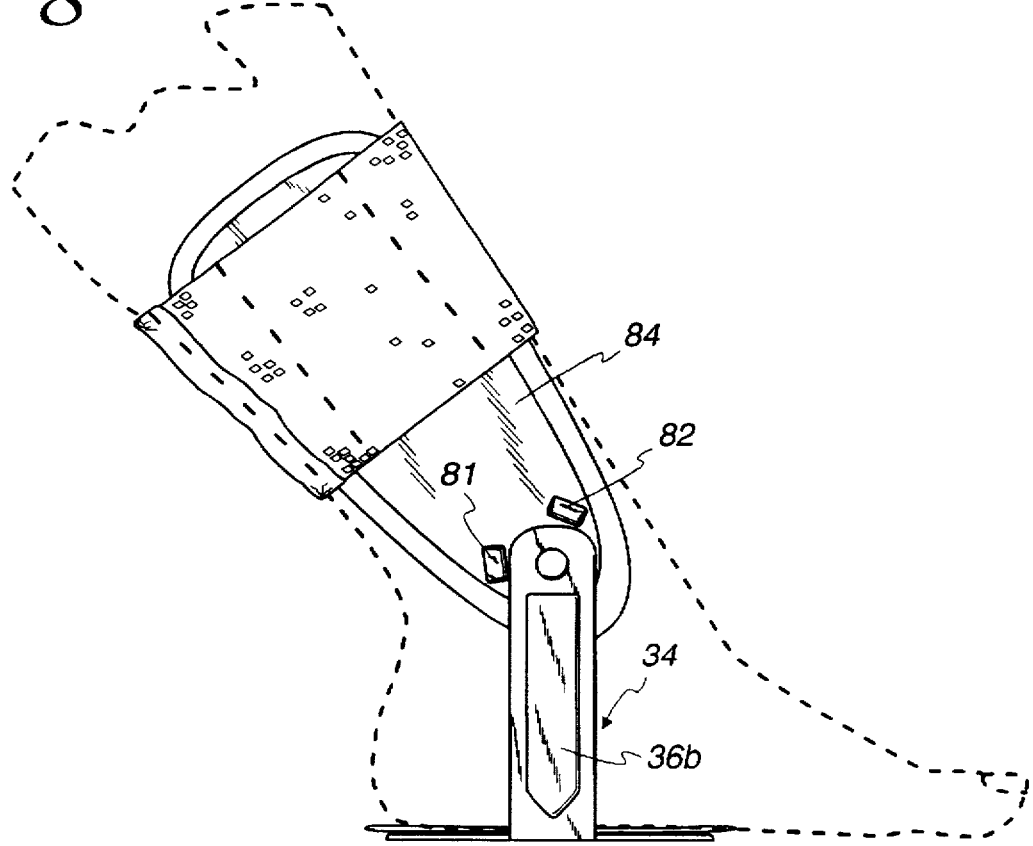
Figure 13:
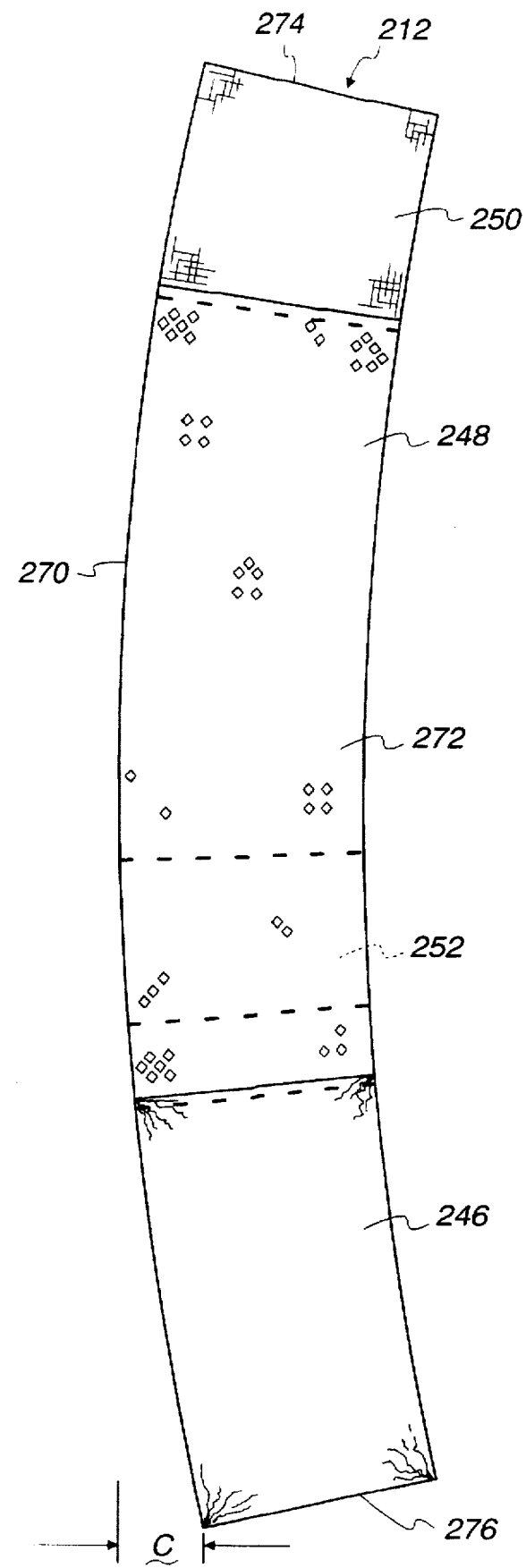

FIG. 8 is a cross-sectional view taken along the line 8—8 of FIG. 4;

FIG. 9 shows a portion of FIG. 6 on an enlarged scale;

FIG. 10 is a side elevational view of the ankle restraint without the strap component;

FIGS. 11 and 12 are side elevational views similar to those of FIGS. 2 and 3, but showing a different stop arrangement; and FIG. 13 is a top plan view of an alternative strap arrangement.

DETAILED DESCRIPTION OF THE PREFERRED EMBODIMENTS

Referring now to the drawings, and initially to FIGS. 1–10, an ankle restraint system according to the principles of the present invention is generally indicated at 10. After manufacture, and when presented to a user, ankle restraint system 10 is comprised of two major components, a strap or cuff assembly generally indicted at 12 and an ankle restraint or articulated stirrup assembly generally indicated at 14. Together, the cuff assembly and stirrup assembly cooperate to limit inversion or eversion injuries when worn on either ankle of a user. The components of the ankle restraint system, and particularly of the articulated stirrup assembly, are contoured to eliminate any sharp or rough edges and to maximize comfort and safety, even during rigorous activities.

As opposed to rehabilitative devices and other appliances adapted for medical treatment, the ankle restraint system of the present invention is constructed to be as lightweight as possible and as non-obtrusive of a user's range and speed of motion, as possible. Accordingly, the ankle restraint system is designed so as to avoid limiting normal ankle motion. However, as will be seen herein, stop members are provided to limit the pivotal movement of the stirrup assembly restricting excessive dorsi flexion or plantar flexion so as to guard against excessive eversion and excessive inversion of the ankle. As those familiar with competitive athletic activities are aware, most sport's related injuries are of the ankle inversion type, where the ankle rolls outward and the outside of the foot rolls under. When exposed to excessive inversion forces, the ankle is twisted in such a manner that the lateral or outer side of the foot is stressed in tension and the medial or inside of the foot undergoes compression along its outer surface. With the ankle restraint of the present invention, these tension and compression forces are transmitted to the articulated stirrup assembly and cuff assembly which cooperate with a user's foot to create a cylinder of protection around a user's ankle.

The articulated stirrup assembly 14 includes a pair of splint assemblies 20 which include a splint plate 22, preferably of a soft, lightweight and semi-rigid, plastic material and a foam pad 24. As can be seen at the upper end of FIG. 1, and in the cross-sectional views of FIGS. 6 and 9, foam pad 24 is secured to splint plate 22 by hook and loop fasteners 26. Despite the presence of a cushioning layer provided by foam pad 24, the contour and condition of the outer edges of splint plate 22 can be immediately felt by a wearer engaged in athletic endeavor, and details of construction are important to the wearer's comfort. Accordingly, the splint plate 22 has a generally convex shape when viewed from the outside so as to conform to the user's anatomy and its outer edges are rounded and smooth.

Preferably, the splint plate 22 is of generally uniform thickness throughout with the concave inner surface of the splint plate being accompanied by a corresponding convex outer surface, as seen in the figures. As will be seen herein, a land portion generally indicated at 30 is provided at the lower end of the splint plate to present a generally flat, planar surface at the point of articulated movement. As can be seen, for example, in FIGS. 1 and 6, splint plate 22 is pivotally secured to struts 36 of a stirrup member generally indicated at 34, with pivot members 38 providing the pivotal connection.

Figure 1:
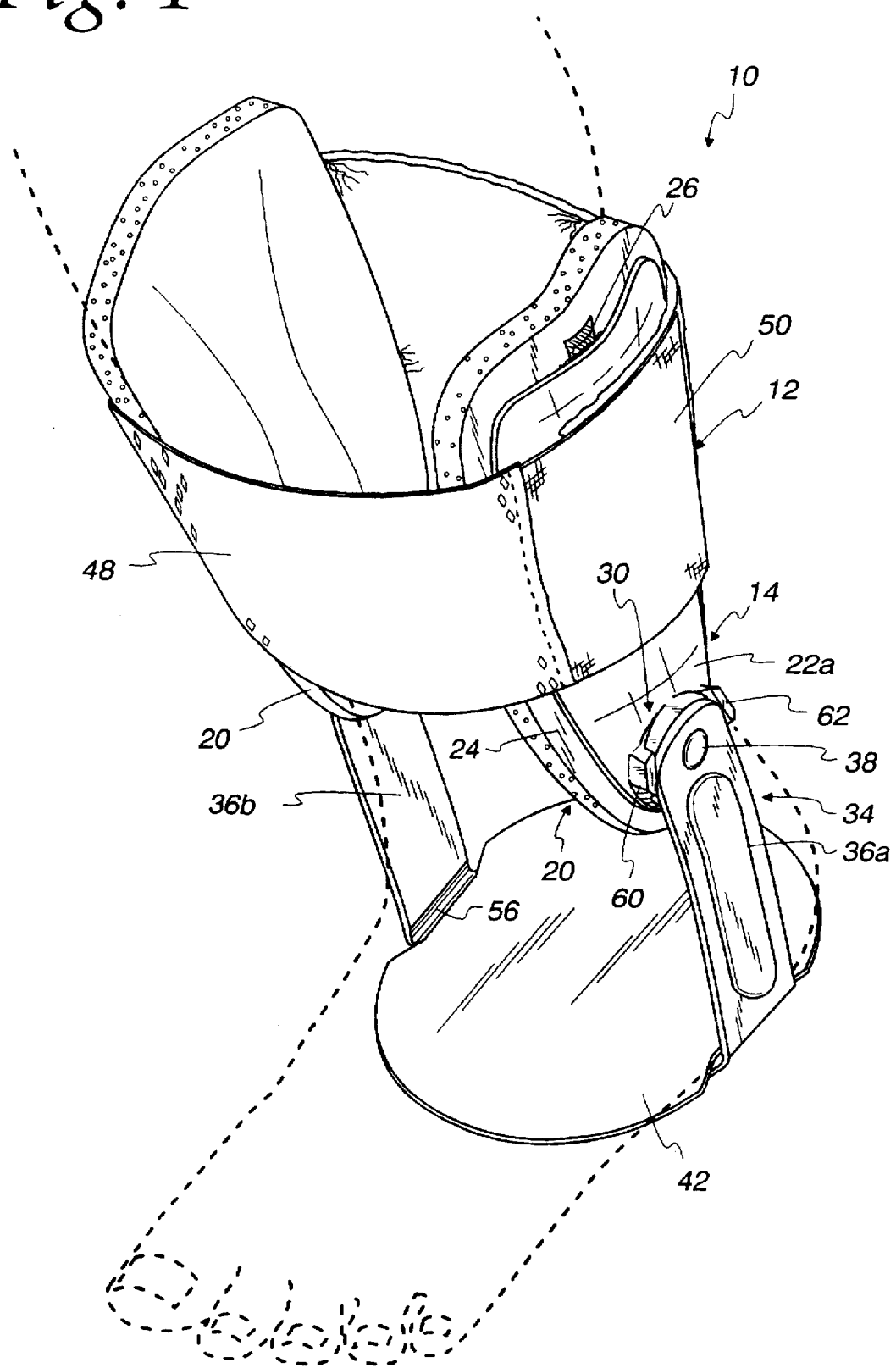
FIG. 1 is a perspective view of an ankle restraint according to the principles of the present invention.

Referring again to FIG. 1, stirrup member 34 includes a sole plate 42, preferably comprising an integral extension of struts 36. In FIG. 1, the outside strut 36a is hinged to an outer sole plate 22a. With reference to FIG. 4, it is generally preferred that the outer strut 36a is slightly shorter than the inner strut 36b such that the inner and outer hinge connections are vertically offset, as indicated in FIG. 4. Accordingly, it is generally preferred that the outer splint plate 22a be made slightly longer than the inner splint plate 22b. The drawings show the ankle restraint worn on the left leg of the user.

According to one aspect of the present invention, the ankle restraint 10 provides a universal fit, and can, without modification, be worn on a user's right leg. When worn on the right leg, the strut 36a and splint plate 22a are located on the outside of a user's leg. Accordingly, with the perspective of FIG. 1 maintained, the toes of a user's right foot would extend to the upper right corner of the figure.

Referring now to FIGS. 5 and 8, cuff assembly 12 is preferably made of flexible, but non-stretchable fabric material. FIG. 5 shows the outer surface of the cuff assembly, including a first panel portion 46 which is double sided, having loop fastener material on both opposed sides, as can be seen, for example, in FIG. 8. A woven, non-stretchable band 48 joins the panel portion 46 to the second end panel portion 50, carrying a hook fastener material on its inner surface, as can be seen in FIG. 8. A panel 52 of loop material is secured to the inner surface of intermediate band 48 as can be seen in FIG. 8 and as outlined by dashed lines in FIG. 5.

Referring now to FIG. 13, an alternative embodiment of the strap or cuff assembly is generally indicated at 212. As will be seen herein, cuff assembly 212 is generally identical in construction to the cuff assembly 12 described above, except for the curved, preferably arcuate shape, which is apparent from FIG. 13. The thickness, numbers of panels and method of assembly is otherwise identical to that of cuff assembly 12. For example, cuff assembly 212 includes a first panel portion 246 which is double-sided, having loop fastener material on both opposed sides. A woven, non-stretchable band 248 joins the panel portion 246 to a second end panel portion 250, carrying a hook fastener material on its inner surface. A panel 252 of looped material is secured to the inner surface (hidden in FIG. 13) of intermediate band 48 as outlined by dashed lines in FIG. 13. Overall, cuff assembly 212 is formed to provide a flexible, but non-stretchable construction. The top and bottom longitudinal edges 270, 272 are curved, preferably arcuate configuration which form generally right angle corners with the minor edges 274, 276. In one commercial example of the preferred embodiment illustrated in FIG. 13, the distance between minor edges 274, 276 is approximately 16 inches with the length of the minor edges being approximately 3 inches. The amount of curvature identified by dimension c in FIG. 13 as measured from the center of cuff assembly 212 ranges between 0.5 and 2 inches, and most preferably between 1 and 1.5 inches. This amount of curvature provides a better non-slip fit when wrapped about the wearer's leg (compared to the arrangement shown in FIG. 5). As a result, both major edges 270, 272 conform more closely to the wearer's anatomy and are in close engagement with the wearer's leg. This provides a tighter, more secure, more rigid fixing or anchoring of the splint plate and has been found to provide adequate fixing or retention of the splint plate when a full range of motion is reached (see for example FIGS. 2 and 3) with continuing pressure being applied to the cooperating stop members. With the "straight" cuff assembly of the type shown in FIG. 5, it is possible that the upper elongate edge will be loosely wrapped about the wearer's leg, as compared to the lower longitudinal edge of the cuff assembly. This more loosely wrapped edge may, with certain wearers, be partly "taken up" as pressure is applied to the stop members after a full range of motion is attained. It is preferable that the wearer experience a rigid restraint with continuing uniform pressure imparted by the cuff assembly when the stop members are fully engaged at an extreme range of permitted motion, rather than having the ankle-reflecting force be resolved, at least partly, in tightening a more loosely wrapped edge of the cuff assembly. It is preferred, once the stop members engage one another at a full range of motion, that the rotatably connected members, the stirrup and splint plate, be rigidly connected to the wearer's anatomy, without further movement, should continuing pressure be applied to the stop members.

Referring to FIG. 8, hook fastener material 56 is secured to the outer surface of splint plate 22a and the outer surface of the opposite splint plate 22b. The inner surface of panel portion 46 is secured to the outside of splint plate 22a and the cuff assembly 12 is wound about the user's leg in a counterclockwise motion, as viewed in FIG. 8. The loop material 52 secured to the inner surface of band 48 engages the hook material 56 on splint plate 22b and, with continued winding about a user's leg, the hook material carried on the inner surface of end portion 50 engages the outer surface of the opposite end portion 46, in the manner illustrated in FIG. 1. Preferably, cuff assembly 12 has a vertical height sufficient to prevent an intentional misalignment of the cuff, once wrapped about a user's leg. In the preferred embodiment, the cuff assembly 12 has a vertical height of approximately three inches and the inner surfaces of end portion 46 and intermediate band 48 which contact the wearer's leg present a non-slip woven raised rib surface having a relatively high coefficient of friction to aid in fixing the cuff about a wearer's leg.

As can be seen in FIG. 1, the upper end of strut 36a is laid on top of the land portion 30 carried at the lower end of splint plate 22a. As can be seen in FIG. 9, a rivet 30 passes through strut 36a and splint plate 22a securing the parts together for relative rotation. The cuff assembly 12 fixes the splint plate against rotation, and, accordingly, the relative rotation about the axis of rivet 38 is localized in movement of the strut. As mentioned, the stirrup member 34 is preferably integrally formed, using suitable, relatively soft and lightweight plastic material. However, the plastic material is chosen such that the hinged portions 56 (see FIG. 1) joining the struts and sole plate are sufficient to maintain the relative orientation of the struts and sole plate during movement by the user, as indicated in FIGS. 2 and 3.

According to one aspect of the present invention, the range of motion of a wearer's ankle is limited in the manner indicated in FIGS. 2 and 3. In order to effectively restrict movement of a wearer's ankle, interference with the pivoting rotation of the struts is initiated upon contact with stop members 60, 62. As can be seen in FIGS. 1 and 10, for example, the upper ends of the struts 36 are rounded with rounded edges 66, preferably with spaced apart circular corners or edges 66a, 66b. If desired, the entire upper edge of the struts can be continuously rounded with a part circular configuration. However, it is generally preferred that the engagement between stop members 60, 62 and the upper free edges of the struts be located to one side or the other of the vertical center line of the struts, i.e., that there be an inactive portion immediately above the rivet 38 as seen in FIG. 10. As one edge of each strut contacts a stop member, a remotely located rounded edge portion also located at the upper end of the strut moves past, preferably in close relationship to the other stop member. In the preferred embodiment, co-action between the strut members and bottom portion of the splint plates at the points of pivotal connection, land surface wiping engagement, full edge contact with the primary stop member and partial edge contact with the secondary stop member cooperate to effectively restrict movement of a user's ankle, beyond defined limits. If desired, however, the secondary stop member (that stop member contacting the rounded edge portion of the strut) may be spaced slightly so as to avoid contact with the strut edge, if desired, although this may lead to increased wear at the point of pivotal connection, over an extended period of time.

Referring to FIG. 7, the outer surface of the splint plate 22 is generally convex, with the inner surface being concave. According to one aspect of the present invention, a land portion 30 is raised above the convex outer surface of the splint plate so as to have an exposed surface of greater curvature than the splint plate and preferably a surface that is flat. An aperture 72 is formed in a central portion of raised land 30 to receive the body of rivet 38. As can be seen, for example, in FIG. 9, the upper portion of strut 36 has a relatively flat inner surface 36' which engages the exposed surface of raised land 30. With reference to FIG. 7, it is generally preferred that the stops 60, 62 extend throughout their length a uniform height above the surface of raised land 30 so as to present stop surfaces 60', 62' to the rounded edge portions 66a, 66b of the struts 36. The face of the stop members is formed with a length ranging between at least 1½ to 2 times the height of the stop face, with the height of the stop face corresponding to the thickness of the edge of the lower member, while insuring substantially complete contact between the face and the edge of the lower member.

As can be seen, for example, in FIGS. 6 and 9, it is generally preferred that the stop faces have a height approximately equal to the thickness of struts 36 adjacent the rivet members 38. Further, as can be seen in FIGS. 6 and 9, it is preferred that the stop members 60, 62 have an increasing depth with increasing distance away from rivet 38. Most preferably, the increased depth of stop member 60, 62 is sufficient such that the exposed faces of the stop members, as seen, for example, in FIG. 10, are generally flat, coplanar with the outer surface of the strut 36. Preferably, the outer surfaces of stop members 60, 62 lying to either side of the exposed, flat faces, are blended with the outer convex surface of the splint plate. Thus, as the struts are rotated back and forth to their end points in the manner shown in FIGS. 2 and 3, a maximum engagement is maintained between the outer edges of the struts and substantially the entire length of the stop faces 60', 62' of the stop members. In this manner, a full resistance is provided at the extreme limits of permitted motion (see FIGS. 2 and 3). Further, a full engagement is maintained with the rivet head, strut surface in contact with the rivet head, strut surface in contact with the raised land portion and strut edges in contact with the stop faces is maintained throughout substantially the entire range of motion which is permitted to a wearer's ankle. This allows the use of lighter, more easily deformed materials without compromising the requisite level of protection. As can be seen by comparing FIGS. 4 and 9, for example, the lower portion of the splint plate outer surface has a complex convex shape being curved in a vertical direction (see FIG. 9) and also in a horizontal direction (see FIG. 4) where the overall outer surface of the splint plate from top to bottom can be seen to have a double reverse curvature. The planar, preferably flat planar, surface of raised land 30 and the mating flat planar surface of strut 36 ensures that alignment of land, strut and stop members needed for effective stopping resistance is maintained throughout the entire range of motion and especially at the outermost limits of motion, despite the speed or direction of forces which may be applied to a wearer's leg.

With reference to FIG. 10, it can be seen that stop members 60, 62 simultaneously contact the upper outer edge of the strut member. As those skilled in the art are aware, the wearer's foot is placed in its most vulnerable position when it is dorsiflexed or "on the toes". Thus, the position indicated in FIG. 2 places a wearer's ankle at its most vulnerable position, as opposed to the position illustrated in FIG. 3. Thus, in this sense, the performance of the rearwardmost stops 60 offer greater protection against injury than the rearward stop 62. However, as mentioned above, it is generally preferred that the ankle restraint provides a universal fit and hence the rearward stops, when placed about the left ankle, become the forward stops when placed about the right ankle. It is generally preferred that the exposed surface of raised land 30 comprise a continuous, flat surface in order to provide assured optimum performance of an ankle restraint employed for a universal fit.

It is generally preferred that the ankle restraint operate to permit a range of motion of 30° dorsi flexion and thereafter absorb the compression forces thereby limiting the injury potential. A value of approximately 30° has been chosen as being appropriate for the limit of normal dorsi flexion. Stops placed at an angle greater than 30° may lose energy absorbing effectiveness. Stops places at less than 30° will restrict normal dorsi flexion and limit natural movement, a condition generally undesirable in athletic competition. However, in particular instances, the forward stops may be placed at angles other than approximately 30°, in order to satisfy individual requirements.

According to one aspect of the present invention, it is desirable that the above-described articulated components be made of non-metallic material. One measure of performance of the chosen plastic material is the ability of that material to function as a motion stop or bumper which limits the relative rotation of the articulated components. Similarly, a compromise may have to be made when selecting non-metallic materials so as to provide an optimum balance between stiffness and impact strength (or toughness). It is preferred, when practicing the present invention, to employ a plastic material having a desired balance between the stiffness and impact strength. Although a maximum stiffness is desired for a stop member in order to provide a definite motion limit not to be exceeded, it is also important that the material chosen be as light as possible consistent with avoiding brittle fracture of the stop members. Accordingly, in order to attain the impact strength required, it is recognized that a certain amount of stiffness may have to be sacrificed. The challenge then is to design stop members which function reliably by exhibiting the impact strength necessary to avoid brittle fracture, while performing adequately despite having a reduced stiffness. In particular, it is preferred in practicing the present invention that the material exhibit a flexural modulus ranging between 150, 000 and 350,000 psi and an impact strength measured by a notched izod value of 2.0 or above. Most preferably, the plastic material employed has a flexural modulus of 200,000 psi and an impact strength measured by a notched izod value of approximately 2.5. Examples of such material are found in various commercial grades of polypropylene plastic materials. While the articulated components could be made of different plastic materials, it is most preferred that a common plastic material be used throughout.

As seen from the above, a lightweight, unobtrusive ankle restraint is provided in an economical form, preferably being made of the same plastic material, throughout. A flat surface land portion is provided for pivotal mating with the upper end of a strut member so as to bring upper edges of the strut member in contact with a pair of stop members located on either side of the land so as to interfere with movement of the strut at its full range of motion. The height of the stop members throughout the length of their strut-engaging face is preferably at least as thick as the strut edge they contact. A full, continuous engagement is preferably established between the strut edges and the stop faces when the desired range of motion is reached. Further, it is preferred that the stop members have a relatively flat planar upper surface and that the stop members be blended into the outer convex surface of the splint plate resulting in increased thickness at the ends of the stop members, and especially at the lower ends of the stop members.

Referring again to FIG. 4, the struts 36a, 36b extend above sole plate 42 in an upwardly and outwardly diverging manner. Preferably, the included angle between the lower ends of struts 36a, 36b and sole plate 42 is 95 degrees, plus or minus 3 degrees. It is generally preferred, in order to maximize wearing comfort, that the upper end of struts 36a, 36b be made to extend in a generally vertical direction. Accordingly, as can be seen in FIG. 4, the upper ends of the struts 36a, 36b are slightly inclined toward each other. As can be seen in FIG. 4, a slight angle is formed between the upper and lower ends of the struts 36a, 36b, preferably by an offsetting amount of 5 degrees plus or minus 3 degrees. In this manner, an improved pivoting joinder between the splint plates and stirrup is provided, while avoiding right angle corners where the struts meet the sole plate.

According to another aspect of the present invention, the upwardly and outwardly diverging shape of the stirrup shown in FIG. 4 provides manufacturing advantages in the form of substantially reduced tooling costs as use of complex compound mold tooling, which would otherwise be required for stirrups formed at right angles, is avoided. Referring to the bottom corners of the stirrup member, in addition to providing an angle greater than 90 degrees, wearing comfort is also improved by the introduction of a radius bend at the stirrup corners. It is recognized that the stirrup could be formed after molding to take on the approximate shape desired. However, such forming requires a separate step in the fabrication process, and additional tooling, requiring additional costs which are prohibitive in certain size markets. Accordingly, it is preferred that the stirrup as shown in FIG. 4 with the angular offsets described, be entirely formed by molding, with post molding forming being avoided.

Referring now to FIGS. 11 and 12, a different, less preferred arrangement is shown with stop members 81, 82 disposed on the outer convex surface of splint plate 84. A stirrup member 34 is preferably identical to that discussed above. However, the stop members 81, 82 are oriented so as to contact edges of the strut 36b only at their lower ends. As can be seen, for example, in FIG. 11, an acute angle gap is formed between stop member 82 and the adjacent edge of strut 36b, while, with reference to FIG. 12, an acute angle gap is formed between stop member 81 and the edge of strut 36b adjacent thereto. In the arrangement shown in FIGS. 11 and 12, a splint plate 84 is not provided with a land, and accordingly the lower end of the splint plate, underlying the upper end of the strut, has a curved convex configuration. As a result, as substantial over pressures are developed at the full ranges of motion shown in FIGS. 11 and 12, forces are developed which twist the strut with respect to the splint plate, causing the edge of the strut to ride over the stop members. While such occurrences have been observed upon generating forces greater than those expected to occur when fitted to a wearer's ankle, it is preferred that the arrangement of FIGS. 1-10 be provided, with the raised flat surface and portion at the lower end of the splint plate, when maximum stopping performance is required of the lightweight ankle restraint.

The drawings and the foregoing descriptions are not intended to represent the only forms of the invention in regard to the details of its construction and manner of operation. Changes in form and in the proportion of parts, as well as the substitution of equivalents, are contemplated as circumstances may suggest or render expedient; and although specific terms have been employed, they are intended in a generic and descriptive sense only and not for the purposes of limitation, the scope of the invention being delineated by the following claims.

What is claimed is:

1. A restraint for limiting movement of the wearer's ankle, comprising:
    a stirrup member with a monolithic one-piece body having a sole plate and a pair of spaced-apart struts upstanding from the sole plate, the struts having upper free ends with a rounded edge portion;
    a pair of leg-engaging splint plates, each having an outer surface and a lower end with a flat surface land portion which extends above the outer surface and the lower end hingedly connected to the upper end of a respective strut, each splint plate carrying a pair of stop members each with stop surfaces, the stop surfaces upwardly and inwardly inclined toward one another, one on either side of the upper free end of said strut;
    each strut having opposed generally co-extensive sides, each side having an edge terminating in said rounded edge portion; and
    the stop surface of one of said stop members to engage one side edge of a strut as the rounded edge portion of the strut moves past the stop surface of the other stop member.

2. The ankle restraint of claim 1 wherein the stop surfaces have a height, measured as a distance above the outer surface of the splint plate, which is at least as great as the thickness of the strut edge, and wherein the stop surfaces have a length extending along the splint plate outer surface which ranges between one and one-half to two and one-half times the height of the stop surface.

3. The ankle restraint of claim 1 wherein the stirrup member and splint plate are formed of a plastic material having a flexural modulus ranging between 150,000 and 350,000 psi and an impact strength with notched izod value at least as great as 2.0.

4. The ankle restraint of claim 3 wherein the plastic material has a flexural modulus of approximately 200,000 and an impact strength of notched izod value of approximately 2.5.

5. The ankle restraint of claim 4 wherein the plastic material is polypropylene.

6. The ankle restraint of claim 1 wherein the strut edges which contact the stop members have a predetermined thickness and the stop surfaces have a height above the splint plate outer surface which is at least as great as the edge thickness.

7. The ankle restraint of claim 1 wherein the stop surfaces extend above the outer surface of the splint plate and have a length extending along the splint plate outer surface, with the stop surfaces engaging edges of the struts substantially continuously throughout the length of the stop surfaces.

8. The ankle restraint of claim 1 wherein the stop members of a splint plate comprising mirror images of one another such that the restraint is adapted for universal fit, so as to be worn either foot, with substantially the same movement limiting performance.

9. The ankle restraint of claim 1 wherein the stop surfaces face toward the flat surface land portion, have a height extending above the flat surface land portion and a length extending generally parallel to the flat surface land portion.

10. The ankle restraint of claim 9 wherein the height of the stop surfaces is substantially constant along the length of the stop surfaces.

11. The ankle restrain of claim 9 wherein the stop surfaces have lower ends which are joined to the flat surface land portion.

12. The ankle restraint of claim 1 wherein the hinged connections of the struts are spaced different distances from the sole plate.

13. The ankle restraint of claim 1 further comprising a strap member of stretch resistant fabric wrapped about the upper ends of the splint plates, and attached to the upper ends of the splint plates by hook and loop fastener material.

14. The ankle restraint of claim 13 further comprising a foam lining carried on the inside surfaces of each splint plate.

* * * * *